United States Patent [19]

Partyka et al.

[11] 4,024,082
[45] May 17, 1977

[54] ANALGESICS

[75] Inventors: Richard Anthony Partyka, Liverpool; Maxwell Gordon, Dewitt, both of N.Y.; Tetsuji Kametani, Sendai; Kazuo Kigasawa, Tokyo, both of Japan

[73] Assignee: Bristol-Myers Company, New York, N.Y. ; by said Richard Anthony Partyka and Maxwell Gordon

[22] Filed: Aug. 19, 1975

[21] Appl. No.: 605,950

[52] U.S. Cl. .................. 260/250 C; 260/DIG. 8; 260/285; 424/250
[51] Int. Cl. .................................. C07D 471/08
[58] Field of Search .......... 260/250 AC, 250 C, 285

[56] References Cited

UNITED STATES PATENTS

| 2,742,500 | 4/1956 | Gregory | 260/559 |
|---|---|---|---|
| 3,452,086 | 6/1969 | Montzka et al. | 260/519 |
| 3,728,347 | 4/1973 | Kigasawa | 260/250 |

OTHER PUBLICATIONS

Eliel, "Stereochemistry of Carbon Compounds," McGraw-Hill, 1962, pp. 49–50, 61.
Greenstein et al., "Chemistry of the Amino Acids," vol. 1, Wiley, 1961, pp. 716–717.
Cassels et al. II, Tetrahedrin, 1966, Suppl. 8, pt. 2, pp. 485–490.
Yamato et al., Tetrahedron, 1966, Suppl. 8, pt. 1, pp. 129–134.
Kametani et al. I, Chem. Pharm. Bull. 16, 296–303, (1968).
Kametani et al. II, J. Med. Chem. 16, p. 301, (1973).
Cassels I, Chem & Industry, 1966, pp. 1635–1636.
Montzka et al. II, J. Organic Chem., 33, pp. 3993–3994, (1964).

*Primary Examiner*—Donald G. Daus
*Assistant Examiner*—Mark L. Berch
*Attorney, Agent, or Firm*—Richard R. Lloyd

[57] ABSTRACT dl-N-Cyclopropylmethyl-3-hydroxy-9-azamorphinan is a compound known to possess analgesic activity that is about twice as potent as pentazocine. Resolution of the compound into its levorotatory and dextrorotatory isomers and subsequent animal testing revealed that l-N-cyclopropylmethyl-3-hydroxy-9-azamorphinan was much more potent than the dl-mixture.

10 Claims, No Drawings

ANALGESICS

BACKGROUND OF THE INVENTION

1. Field of the Invention

This invention relates to the resolution of dl-N-cyclopropylmethyl-3-hydroxy-9-azamorphinan into its essentially pure optical isomers.

2. Description of the Prior Art

A. The compound dl-N-cyclopropylmethyl-3-hydroxy-9-azamorphinan and the pharmaceutically acceptable salts thereof are described in U.S. Pat. No. 3,728,347, which patent issued on Apr. 17, 1973.

B. Initial pharmacological data was published on dl-N-cyclopropylmethyl-3-hydroxy-9-azamorphinan in J. Med. Chem. 16, 301 (1973). The paper reports the compound is about twice as active as pentazocine.

SUMMARY OF THE INVENTION

A process has been discovered for the resolution of the racemic mixture of N-Cyclopropylmethyl-3-hydroxy-9-azamorphinan, a compound having the formula

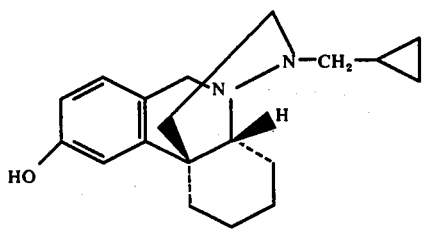

into its essentially pure dextrorotatory and levorotatory isomers.

Complete Disclosure dl-N-Cyclopropylmethyl-3-hydroxy-9-azamorphinan is a compound described and claimed in U.S. Pat. No. 3,728,347, which patent issued on Apr. 17, 1973. The compound is described to have a remarkable analgesic activity as strong as that possessed by morphine. The compound is further described as lacking opiate dependence liability, and as such it has substantial potential as a therapeutic analgesic agent. This reported activity, as is generally the case, was based upon data accummulated in mice and other lower species of mammals. The activity found in mice was confirmed in clinical studies in humans.

For the purpose of improving the activity of the compound as to its potency, side effects and/or toxicity to mammals, including man, attempts were initialed to resolve dl-KMG-86 into its essentially pure levorotatory and dextrorotatory isomers. However, all initial attempts using those commonly employed resolving agents known to the art failed to achieve resolution.

It was, therefore, an object of the present invention to resolve dl-KMG-86 into its essentially pure dextrorotatory and levorotatory isomers. The object of the invention was achieved using either of the three resolving agents, namely, (2R:3R)-2'-nitrotartranilic acid to isolate the dextrorotatory isomer with the levo isomer being recovered from the mother liquor. Alternatively one may use O,O-dibenzoyl-d-tartaric acid or (2S:3S)-2'-nitrotartranilic acid to isolate the levorotatory isomer.

Resolution of dl-KMG-86 produced l-N-cyclopropylmethyl-3-hydroxy-9-azamorphinan (l-KMG-86) and d-N-cyclopropylmethyl-3-hydroxy-9-azamorphinan (d-KMG-86).

The dl-KMG-86, d-KMG-86 and l-KMG-86 were all screened for their biological activity by the assays described in the reference J. Med. Chem. 16, 301 (1973). All three compounds were screened for their analgesic activity by the acetic acid induced stretching method of R. Kosta, Fed. Proc., Fed. Amer. Soc. Exp. Biol., 18, 412 (1959). Male albino mice dd strain (18.0–22.0 g.) were used. After the compounds were administered subcutaneously to five groups of animals consisting of ten mice per group, the effective ratio until 60 minutes was examined and the effective dose in 50% of the mice ($ED_{50}$) was calculated by the Lichfield-Wilcoxin method [J. T. Lichfield and F. Wilcoxin, J. Pharmacol., 96, 99 (1949)]. The ability of these compounds to antagonize morphine analgesia ($ED_{100}$, 16 mg/kg subcutaneously) was calculated by the Haffner method [F. Haffner, Deut. Med. Wochenschr., 55, 731 (1929)], in which ten male mice dd strain per group were used.

The results of both tests are summarized in Tables I and II respectively.

TABLE I

| ANALGESIC ACTIVITY | | | |
|---|---|---|---|
| Effective Ratio and $ED_{50}$ by Lichfield-Wilcoxin Method | | | |
| | | $ED_{50}$, Mean Value | 95% Fiducial limit |
| Method | Compd. | mg/kg | mg/kg |
| Stretching | dl-KMG-86 | 1.63 | 0.99 – 2.7 |
| | d-KMG-86 | ca. 80 | |
| | l-KMG-86 | 0.45 | 0.22 – 0.91 |
| | Pentazocine | 2.40 | 1.56 – 3.70 |

Table I shows that the l-isomer is about 3.5 fold more potent than the dl-mixture. It is undeniable that l or d-isomers are to a certain extent more potent than their dl-mixture, but it is also true that such a great increase in potency, as shown above, cannot be readily anticipated until the compounds are resolved and screened. It is to be noted also that the l-isomer has no substantial side effects or toxicity.

TABLE II

| Comparison of the Antagonistic Effect of Morphine Analgesia by Haffner Method | | |
|---|---|---|
| | Antagonist Dose | |
| Compd. | ($AD_{50}$) | 95% Fiducial limit |
| | mg/kg, S. C. | mg/kg |
| dl-KMG-86 | 4.70 | 4.55 – 4.87 |
| d-kmg-86 | 20 | |
| l-KMG-86 | 2.20 | 1.80 – 3.30 |
| Levallorphan | 0.24 | 0.16 – 0.36 |

A preferred embodiment of the present invention is the essentially pure levorotatory (−) and dextrorotatory (+) isomers of 3-hydroxy-9-azamorphinan or N-cyclopropylmethyl-3-hydroxy-9-azamorphinan; or a nontoxic pharmaceutically acceptable acid addition salt thereof.

A most preferred embodiment is the essentially pure levorotatory (−) of 3-hydroxy-9-azamorphinan or N-cyclopropylmethyl-3-hydroxy-9-azamorphinan; or a nontoxic pharmaceutically acceptable acid addition salt thereof.

For the purpose of this disclosure, "a nontoxic pharmaceutically acceptable acid addition salt" shall mean a mono- or disalt formed by the interaction of one or two moles of a pharmaceutically acceptable acid per mole of (+) or (−)-KMG-86. Included among these acids are acetic, hydrochloric, sulfuric, maleic, phosphoric, nitric, hydrobromic, ascorbic, malic, citric and tartaric acid, and those other acids commonly used to make salts of amine containing pharmaceuticals.

Another preferred embodiment is the process for the resolution of (+)-N-cyclopropylmethyl-3-hydroxy-9-azamorphinan into its essentially pure (+) and (−) isomers, which process comprises the consecutive steps of A. dissolving the racemic mixture and d-O,O-dibenzoyltartaric acid or (2R:3R)-2′-nitrotartranilic acid, or (2S:3S)-2′-nitrotartranilic acid in a ratio of 0.5 to 1.5 moles of acid per mole of azamorphinan, in a polar solvent to produce the diastereoisomer salt of the (+) or (−) azamorphinan, which is collected, B. concentrating the mother liquors from step A and adding d-O,O-dibenzoyltartaric acid or (2R:3R)-2′-nitrotartranilic acid or (2S:3S)-2′-nitrotartranilic acid to the solution to produce the diastereoisomer salt not collected in step A, which is collected, and C. treating separately the (+) and (−) diastereoisomer salts isolated in steps A and B with a base to liberate the essentially pure (+) and (−) optical isomers, which are collected.

A most preferred embodiment is the process for the resolution of (+)-N-cyclopropylmethyl-3-hydroxy-9-azamorphinan into its essentially pure (−) and (+) optical isomers, which process comprises the consecutive steps of A. dissolving the racemic mixture and (2R:3R)-2′-nitrotartranilic acid, in a ratio of about 0.5 mole of tartranilic acid per mole of azamorphinan, in a polar solvent selected from the group consisting of acetone, water, ethanol, methanol, isopropanol, and the like, or a mixture thereof, to produce the diastereoisomer salt of (+)-N-cyclopropylmethyl-3-hydroxy-9-azamorphinan as a crystalline solid which is collected by filtration;

B. concentrating the (−)-isomer azamorphinan enriched mother liquor in vacuo and adding d-O,O-dibenzoyltartaric acid, in a ratio of about 1 to 1.5 mole of acid per theoretical molar amount of (−)-isomer in the mother liquors to produce the diastereoisomer salt of (−)-N-cyclopropylmethyl-3-hydroxy-9-azamorphinan, which is collected; and C. treating separately the diastereoisomer salts obtained in steps A and B with a base to liberate the essentially pure (+) and (−)-optical isomers of N-cyclopropylmethyl-3-hydroxy-9-azamorphinan.

Also a preferred embodiment is the process for the resolution of (+)-N-cyclopropylmethyl-3-hydroxy-9-azamorphinan into its essentially pure (−) and (+) optical isomers, which process comprises the consecutive steps of A. dissolving the racemic mixture and (2R:3R)-2′-nitrotartranilic acid, in a ratio of about 0.5 mole of tartranilic acid per mole of azamorphinan, in a polar solvent selected from the group consisting of acetone, water, ethanol, methanol, isopropanol, and the like, or a mixture thereof, to produce the diastereoisomer salt of (+)-N-cyclopropylmethyl-3-hydroxy-9-azamorphinan as a crystalline solid which is collected by filtration;

B. concentrating the (−)-isomer azamorphinan enriched mother liquor in vacuo and adding (2S:3S)-2′-nitrotartranilic acid, in a ratio of about 0.5 to 0.6 mole of acid per theoretical molar amount of (−)-isomer in the mother liquors to produce the diastereoisomer salt of (−)-N-cyclopropylmethyl-3-hydroxy-9-azamorphinan, which is collected; and C. treating separately the diastereoisomer salts obtained in steps A and B with a base to liberate the essentially pure (+) and (−)-optical isomers of N-cyclopropylmethyl-3-hydroxy-9-azamorphinan.

Another most preferred embodiment is the process for the resolution of (+)-N-cyclopropylmethyl-3-hydroxy-9-azamorphinan into its essentially pure (−) and (+) optical isomers, which process comprises the consecutive steps of A. dissolving the racemic mixture and (2R:3R)-2′-nitrotartranilic acid, in a ratio of about 0.5 mole of tartranilic acid per mole of azamorphinan, in a polar solvent selected from the group consisting of acetone, water, ethanol, methanol, isopropanol, or a mixture thereof, to produce the diastereoisomer salt of (+)-N-cyclopropylmethyl-3-hydroxy-9-azamorphinan as a crystalline solid which is collected by filtration;

B. repeating the procedure of step A, adding an additional 0.2 to 0.3 moles of the tartranilic acid to the mother liquor from step A to produce a second crop of crystals which is collected by filtration; and C. evaporating the mother liquors from step B to dryness, dissolving the residue in a water immiscible solvent, washing the resultant solution with a base and water, and evaporating the water immiscible solvent to produce the essentially pure (−)-N-cyclopropylmethyl-3-hydroxy-9-azamorphinan.

Still another most preferred embodiment is the process for the resolution of (+)-N-cyclopropylmethyl-3-hydroxy-9-azamorphinan into its essentially pure (−)-optical isomer, which process comprises the consecutive steps of A. dissolving the racemic mixture and d-O,O-dibenzoyltartaric acid, in a ratio of 1 to 1.2 moles of acid per mole of azamorphinan, in a polar organic solvent to produce the diastereoisomer salt of the (−)-optical isomer as an oil or crystalline solid, which is collected and crystallized from isopropanol, methanol or ethanol; and B. treating the diastereoisomer salt isolated in step A with a base to liberate the essentially pure (−)-optical isomer, which is collected.

Still another most preferred embodiment is the process for the resolution of (+)-N-cyclopropylmethyl-3-hydroxy-9-azamorphinan into its essentially pure (−)-optical isomer, which process comprises the consecutive steps of A. dissolving the racemic mixture and (2S:3S)-2′-nitrotartranilic acid, in a ratio of 0.5 to 0.6 moles of acid per mole of azamorphinan, in a polar organic solvent to produce the diastereoisomer salt of the (−)-optical isomer as a crystalline solid, which is collected and recrystallized from isopropanol, methanol or ethanol; and B. treating the diastereoisomer salt isolated in step A with a base to liberate the essentially pure (−)-optical isomer, which is collected.

Another preferred embodiment is the process for the resolution of (+)-3-hydroxy-9-azamorphinan into its essentially pure (−) and (+) optical isomers, which process comprises the consecutive steps of A. dissolving the racemic azamorphinan and (2R:3R)-4′-nitrotartranilic acid, in a ratio of about 0.5 mole of acid per mole of azamorphinan, in a polar solvent to produce the diastereoisomer salt of the (+)-optical isomer as crystals which are collected;

B. repeating the procedure of step A, adding an additional 0.2 to 0.3 moles of the tartranilic acid to the mother liquors from step A to produce a second crop of crystals, which is collected; and C. evaporating the mother liquors from step B to dryness in vacuo, dissolving the residue in a water immiscible solvent, washing the resultant solution with a base and water, and evaporating the water immiscible solvent to produce the essentially pure (−)-optical isomer.

DESCRIPTION OF THE PREFERRED EMBODIMENTS

EXAMPLE 1

Resolution of (+)-N-Cyclopropylmethyl-3-hydroxy-9-azamorphinan into its optical isomers A. A solution of 2.0 g of dl-N-cyclopropylmethyl-3-hydroxy-9-azamorphinan and 2.4 g of d-O,O-dibenzoyltartaric acid in 300 ml of acetone was left at room temperature overnight. The separated oil was washed with $Et_2O$ and crystallized from iso-PrOH while cooling in refrigerator. The crystals were separated and recrystallized from iso-PrOH to give 2.0 g of 1-N-cyclopropylmethyl-3-hydroxy-9-azamorphinan d-O,O-dibenzoyltartrate as colorless needles; mp 158–160°.

The diastereoisomer salt was treated with 28% $NH_4OH$ and extracted with $Et_2O$. The extract was washed ($H_2O$), dried ($MgSO_4$) and evaporated to give 0.9 g (90%) of 1-N-cyclopropylmethyl-3-hydroxy-9-azamorphinan as colorless needles; mp 151°–153° (from $Et_2O$); $[\alpha]_D^{27}$: −102.4° (c=0.025, MeOH, 1=o1 dm).

The mother liquor from the above salt formation was concentrated to dryness. The residue was basified with 28% $NH_4OH$ and extracted with $Et_2O$. The extract was washed ($H_2O$), dried ($MgSO_4$) and evaporated to give a crystalline residue, which was recrystallized from $Et_2O$ to give 0.76 g (76.0%) of d-N-cyclopropylmethyl-3-hydroxy-9-azamorphinan as colorless needles; mp 151°–153°; $[\alpha]_D^{27}$: +101.6° (c=0.025, MeOH, 1=0.1 dm).

B. A solution of 3.0 g of dl-N-cyclopropylmethyl-3-hydroxy-9-azamorphinan and 1.36 g of (2R:3R)-2'-nitrotartranilic acid in 50 ml of 90% EtOH was heated in order to dissolve the undissolved material on a water bath and the resulting clear solution was set aside in refrigerator overnight. The separated yellow crystals were filtered and basified with 28% $NH_4OH$, a solution of which was extracted with $CHCl_3$. The extract was washed ($H_2O$), dried ($MgSO_4$) and evaporated to give 0.5 g (33.3%) of (+)-N-cyclopropylmethyl-3-hydroxy-9-azamorphinan as colorless needles; mp 151°–153° (from $Et_2O$); which was identical with the authentic sample from (A) in comparisons of mp, ir spectrum and optical rotation.

To the mother liquor in the above salt formation 0.6 g of (2R:3R)-2'-nitrotartranilic acid was added and the separated solid was filtered off. The filtrate was condensed to leave a residue which was dissolved in $CHCl_3$. The $CHCl_3$ solution was washed ($H_2O$), dried ($MgSO_4$), and evaporated to afford 0.7 g (43.3%) of (−)-N-cyclopropylmethyl-3-hydroxy-9-azamorphinan as colorless needles; mp 151°–153° (from $Et_2O$); which was identical with the authentic sample from (A) in comparisons of mp, ir spectrum and optical rotation.

EXAMPLE 2

Resolution of (+)-3-Hydroxy-9-azamorphinan into its optical isomers

A solution of 3.0 g of dl-3-hydroxy-9-azamorphinan and 1.7 g of (2R:3R)-2'-nitrotartranilic acid in 50 ml of 90% EtOH was heated in order to dissolve the undissolved material and the resulting clear solution was set aside overnight in refrigerator. The separated substance was collected by filtration and 2.2 g of the resulting yellow crystals were basified with 28% $NH_4OH$ and extracted with $CHCl_3$. The extract was washed ($H_2O$), dried ($MgSO_4$) and evaporated to afford 1.0 g (66.7%) of (30)-3-hydroxy-9-azamorphinan as colorless needles; mp 244°–246° (from isoPrOH); $[\alpha]_D^{26}$: +34.0° (c=0.01, DMF, 1-0.1 dm).

To the mother liquor in the above salt formation 0.3 g of (2R:3R)-2'-nitrotartranilic acid was added and the separated solid was filtered off. The solvent was removed by evaporation of the above filtrate and the residue was dissolved in $CHCl_3$. The organic layer was washed (10% $NH_4OH$ and then $H_2O$), dried ($MgSO_4$), and evaporated to give 1.2 g (80.0%) of (−)-3-hydroxy-9-azamorphinan as colorless needles; mp 244°–246° (from iso-PrOH); $[\alpha]_D^{26}$: (−) 34.0° (c=0.01, DMF, $d$ = 0.1 dm).

EXAMPLE 3

Preparation of (+)-N-cyclopropylmethyl-3-hydroxy-9-azamorphinan (d-KMG-86) from +-3-hydroxy-9-azamorphinan To a suspension of 0.6 g of (+)-3-hydroxy-9-azamorphinan in 50 ml of $Et_2O$ and 20 ml of 20% NaOH aq. solution was added 1.0 g of cyclopropylcarbonyl chloride with stirring at room temperature. After stirring for 1 hr., the organic layer was washed (10% NaOH and then $H_2O$), dried ($K_2CO_3$), and evaporated to give an oil, which was triturated with $Et_2O$-pet. ether to form a solid. Recrystallization of this from $Et_2O$ afforded 0.5 g (53.5%) of (+)-N-cyclopropylcarbonyl-3-cyclopropylcarbonyloxy-9-azamorphinan as colorless plates; mp 144°–145.5.°.

A mixture of 0.4 g of this amide and 0.3 g of $LiAlH_4$ in 50 ml of dry dioxane was refluxed for 6 hrs., and the excess of $LiAlH_4$ was decomposed with water. After separation of an inorganic material, the filtrate was dried ($MgSO_4$) and evaporated to give 0.25 g (79.7%) of (+)-N-cyclopropylmethyl-3-hydroxy-9-azamorphinan as colorless needles; mp 151°–153° (from $Et_2O$); which was identical with the authentic sample in comparisons of mp, ir spectrum and optical rotation.

EXAMPLE 4

Preparation of (−)-N-cyclopropylmethyl-3-hydroxy-9-azamorphinan (l-KMG-86) from (−)-3-hydroxy-9-azamorphinan.

Substitution in the procedure of example 3 for the (+)-3-hydroxy-9-azamorphinan used therein of an equimolar quantity of (−)-3-hydroxy-9-azamorphinan produced the title compound; m.p. 151°–153° C; with identical characteristics of the same compound produced in example 1.

EXAMPLE 5

Resolution of (+)-N-Cyclopropylmethyl-3-hydroxy-9-azamorphinan into (−)-N-cyclopropylmethyl-3-hydroxy-9-azamorphinan.

dl-N-cyclopropylmethyl-3-hydroxy-9-azamorphinan (3.0 g) and 1.5 grams of (2S:3S)-2'-nitrotartranilic acid in 50 ml of 90% ethanol is heated to dissolve all the solids. The resulting solution is cooled in a refrigerator overnight. Yellow crystals form which are the diastereoisomer salt of (−)-N-cyclopropylmethyl-3-hydroxy-9-azamorphinan. The crystals are collected by filtration. The crystals are covered with 60 ml of chloroform and the mixture is treated with 28% NH₄OH until the aqueous phase remains distinctly basic. The solids dissolve and the chloroform extract is collected, washed with water and dried over MgSO₄. The chloroform solution is filtered off of the MgSO₄, and evaporated to dryness in vacuo. The residue is crystallized from ether to produce the desired (−)-isomer.

We claim:

1. A process of resolving (+)-N-cyclopropylmethyl-3-hydroxy-9-azamorphinan into its essentially pure (+) and (−) optical isomers, which process comprises the consecutive steps of
   A. dissolving the racemic mixture and d-O,O-dibenzoyltartaric acid or (2R:3R)-2'-nitrotartranilic acid or (2S:3S)-2'-nitrotartranilic acid, in a ratio of about 0.5 to 1.5 moles of acid per mole of azamorphinan, in a polar solvent selected from the group consisting of methanol, ethanol, isopropanol and acetone, to produce the diastereoisomer salt of the (+) or (−)-azamorphinan, which is collected;
   B. concentrating the mother liquors from step A and adding additional d-O,O-dibenzoyltartaric acid or (2R:3R)-2'-nitrotartranilic acid or (2S:3S)-2'-nitrotartranilic acid to the solution to produce the diastereoisomer salt of the optical isomer not collected in step A, which is collected; and
   C. treating separately the essentially pure diastereoisomer salts isolated in steps A and B with a base to liberate the essentially pure (+) and (−) optical isomers.

2. The process of claim 1 which process comprises the consecutive steps of
   A. dissolving the racemic mixture and (2R:3R)-2'-nitrotartranilic acid, in a ratio of about 0.5 mole of tartranilic acid per mole of azamorphinan, in a polar solvent selected from the group consisting of acetone, water, ethanol, methanol, isopropanol, or a mixture thereof to produce the diastereoisomer salt of (+)-N-cyclopropylmethyl-3-hydroxy-9-azamorphinan as a crystalline solid which is collected by filtration;
   B. concentrating the (−)-isomer azamorphinan enriched mother liquor and adding d-O,O-dibenzoyltartaric acid, in a ratio of about 1 to 1.5 mole of acid per theoretical molar amount of (−)-isomer in the mother liquors, to produce the diastereoisomer salt of (−)-N-cyclopropylmethyl-3-hydroxy-9-azamorphinan, which is collected; and
   C. treating separately the diastereoisomer salts obtained in steps A and B with a base to liberate the essentially pure (+) and (−) optical isomers of N-cyclo-propylmethyl-3-hydroxy-9-azamorphinan.

3. The process of claim 1 which process comprises the consecutive steps of
   A. dissolving the racemic mixture and (2R:3R)-2'-nitrotartranilic acid, in a ratio of about 0.5 mole of tartranilic acid per mole of azamorphinan, in a polar solvent selected from the group consisting of acetone, water, ethanol, methanol, isopropanol, or a mixture thereof, to produce the diastereoisomer salt of (+)-N-cyclopropylmethyl-3-hydroxy-9-azamorphinan as a crystalline solid which is collected by filtration;
   B. concentrating the (−)-isomer azamorphinan enriched mother liquor in vacuo and adding (2S:3S)-2'-nitrotartranilic acid, in a ratio of about 0.5 to 0.6 mole of acid per theoretical molar amount of (−)-isomer in the mother liquors to produce the diastereoisomer salt of (−)-N-cyclopropylmethyl-3-hydroxy-9-azamorphinan, which is collected; and
   C. treating separately the diastereoisomer salts obtained in steps A and B with a base to liberate the essentially pure (+) and (−) optical isomers of N-cyclopropylmethyl-3-hydroxy-9-azamorphinan.

4. The process of claim 1 for the preparation of essentially pure (−)-N-cyclopropylmethyl-3-hydroxy-9-azamorphinan, which process comprises the consecutive steps of
   A. dissolving the racemic mixture and (2R:3R)-2'-nitrotartranilic acid, in a ratio of about 0.5 mole of tartranilic acid per mole of azamorphinan, in a polar solvent selected from the group consisting of acetone, water, ethanol, methanol, isopropanol, or a mixture thereof, to produce the diastereoisomer salt of (+)-N-cyclopropylmethyl-3-hydroxy-9-azamorphinan as a crystalline solid which is collected by filtration;
   B. repeating the procedure of step A, adding an additional 0.2 to 0.3 moles of the tartranilic acid to the mother liquor from step A to produce a second crop of crystals which is collected by filtration; and
   C. evaporating the mother liquor from step B to dryness, dissolving the residue in a water immiscible solvent, washing the resultant solution with a base and water, and evaporating the water immiscible solvent to produce the essentially pure (−)-N-cyclopropylmethyl-3-hydroxy-9-azamorphinan.

5. The process of claim 1 for the preparation of essentially pure (−)-N-cyclopropylmethyl-3-hydroxy-9-azamorphinan, which process comprises the consecutive steps of
   A. dissolving the racemic mixture and d-O,O-dibenzoyltartaric acid, in a ratio of 1 to 1.2 moles of acid per mole of azamorphinan, in a polar organic solvent selected from the group consisting of methanol, ethanol, isopropanol and acetone, to produce the diastereoisomer salt of the (−) optical isomer as an oil or crystalline solid, which is collected and crystallized from isopropanol, methanol or ethanol; and
   B. treating the diastereoisomer salt isolated in step A with a base to liberate the essentially pure (−)-N-cyclopropylmethyl-3-hydroxy-9-azamorphinan.

6. The process for the resolution of (+)-N-cyclopropylmethyl-3-hydroxy-9-azamorphinan into its essentially pure (−)-optical isomer, which process comprises the consecutive steps of
   A. dissolving the racemic mixture and (2S:3S)-2'-nitrotartranilic acid, in a ratio of 0.5 to 0.6 moles of acid per mole of azamorphinan, in a polar organic solvent to produce the diastereoisomer salt of the (−)-optical isomer as a crystalline solid, which is collected and recrystallized from isopropanol, methanol or ethanol; and B. treating the diastereoisomer salt isolated in step A with a base to liberate the essentially pure (−)-optical isomer, which is collected.

7. The process of claim 1 for the resolution of (+)-3-hydroxy-9-azamorphinan into its essentially pure (+) and (−) optical isomers, which process comprises the consecutive steps of A. dissolving the racemic 3-hydroxy-9-azamorphinan and (2R:3R)-4′-nitrotartranilic acid, in a ratio of about 0.5 mole of acid per mole of azamorphinan in a polar solvent selected from the group consisting of methanol, ethanol, isopropanol and acetone to produce the diastereoisomer salt of (+)-3-hydroxy-9-azamorphinan, which is collected.

B. repeating the procedure of step A, adding an additional 0.2 to 0.3 moles of the tartranilic acid to the mother liquors from step A to produce a second crop of crystals, which is collected; and C. evaporating the mother liquors from step B to dryness, dissolving the residue in a water immiscible solvent, selected from the group consisting of chloroform, methylene chloride, diethyl ether, washing the resultant solution with a base and water, and evaporating the water immiscible solvent to produce the essentially pure (−)-3-hydroxy-9-azamorphinan.

8. l-N-Cyclopropylmethyl-3-hydroxy-9-azamorphinan d-O,O-dibenzoyltartrate.

9. d-N-Cyclopropylmethyl-3-hydroxy-9-azamorphinan (2R:3R)-2′-nitrotartranilate.

10. l-N-Cyclopropylmethyl-3-hydroxy-9-azamorphinan (2S:3S)-2′-nitrotartranilate.

* * * * *

UNITED STATES PATENT AND TRADEMARK OFFICE
CERTIFICATE OF CORRECTION

PATENT NO. : 4,024,082
DATED : May 17, 1977
INVENTOR(S) : Richard A. Partyka, et al.

It is certified that error appears in the above-identified patent and that said Letters Patent are hereby corrected as shown below:

In column 3, line 8, "(+)" should read --($\pm$)--.
In column 3, line 28, "(+)" should read --($\pm$)--.
In column 3, line 52, "(+)" should read --($\pm$)--.
In column 4, line 8, "(+)" should read --($\pm$)--.
In column 4, line 31, "(+)" should read --($\pm$)--.
In column 4, line 46, "(+)" should read --($\pm$)--.
In column 4, line 61, "(+)" should read --($\pm$)--.
In the title of Example 1, "(+)" should read --($\pm$)--.
In the title of Example 2, "(+)" should read --($\pm$)--.
In the title of Example 5, "(+)" should read --($\pm$)--.

In Claim 1, in the first line thereof "(+)" should read --($\pm$)--.

In Claim 6, in the first line thereof "(+)" should read --($\pm$)--.

In Claim 7, in the first line thereof "(+)" should read --($\pm$)--.

Signed and Sealed this thirtieth Day of August 1977

[SEAL]

Attest:

RUTH C. MASON
Attesting Officer

C. MARSHALL DANN
Commissioner of Patents and Trademarks